United States Patent [19]
Bowers

[11] 4,030,510
[45] June 21, 1977

[54] STANDBY HEART PACER

[75] Inventor: David L. Bowers, West Allis, Wis.

[73] Assignee: General Electric Company, Schenectady, N.Y.

[22] Filed: Nov. 5, 1975

[21] Appl. No.: 628,956

Related U.S. Application Data

[63] Continuation of Ser. No. 18,051, March 10, 1970, abandoned.

[52] U.S. Cl. .......................................... 128/419 PG
[51] Int. Cl.² .......................................... A61N 1/36
[58] Field of Search ............ 128/419 PG, 421, 422, 128/423

[56] References Cited
UNITED STATES PATENTS

| | | | |
|---|---|---|---|
| 3,528,428 | 9/1970 | Berkovits | 128/419 PG |
| 3,656,487 | 4/1972 | Gobeli | 128/419 PG |
| 3,688,776 | 9/1972 | Kenny | 128/419 PG |

FOREIGN PATENTS OR APPLICATIONS 826,766  1/1960  United Kingdom ......... 128/419 PG

OTHER PUBLICATIONS

Leatham et al., "The Lancet", vol. 271, Dec. 8, 1956, pp. 1185–1189.
Firth–Cleveland Mfg. Publication No. FCI–955, Issue 2, Jan. 1961, 28 pp.

*Primary Examiner*—William E. Kamm
*Attorney, Agent, or Firm*—Ralph G. Hohenfeldt

[57] ABSTRACT

A pace pulse generator connects to the heart for stimulating it as required. Heart action due to both natural and artificially stimulated beats is detected. Detected signals are variously processed and stored in a hysteresis circuit which serves as a memory as to the last naturally stimulated heart beat. With the hysteresis circuit set to operate in the negative mode, the hysteresis circuit will wait to determine if a natural beat occurs in a predetermined period of time. If no natural beat occurs, the hysteresis circuit turns on the pulse generator to furnish one or more artificial stimulating pulses until the circuit is reset by occurrence of a naturally stimulated heart beat. With the hysteresis circuit set to operate in the positive mode, the hysteresis circuit similarly waits to determine if a natural beat occurs in a predetermined period of time, but this predetermined period of time is less than the period between the constant rate pulses which are produced by the pulse generator.

9 Claims, 3 Drawing Figures

Inventor
David L. Bowers
By Ralph D. Hohenfeldt

STANDBY HEART PACER

This is a continuation, of application Ser. No. 18,051, filed Mar. 10, 1970 now abandoned.

BACKGROUND OF THE INVENTION

Electric heart pacers, commonly called artificial Pacemakers, have been used in patients whose hearts have defective electric conduction systems. An example of such defect is known as heart block where the natural pacemaker on the atrium generates its signal but the signal does not always get through the conductive bundle to stimulate contraction of the ventricle. Although the ventricle may not receive natural signal, it will usually contract ultimately in response to its own escape mechanism. This intrinsic contraction of the ventricle occurs at a lower rate than the atrial contraction, in which case, the patient's blood circulation is inadequate.

Artificial electric heart pacers have been used as a partial remedy for the aforegoing condition. The first generation of pacers were nothing more than fixed rate pulse generators, which connected to the ventricle for causing it to contract at a fixed rate. It was soon observed, however, that on occasion the natural electric signals of the heart were restored and that competition between the natural and artificial pacers occurred, sometimes with undesirable physiological consequences both to patient safety and cardiac efficiency. In U.S. Pat. No. 3,241,556, F. Zacouto, proposed a remedy for this situation in the form of a pacer which only stimulated the ventricle on demand. This patent uses an external electrocardiograph sensor which, in conjunction with suitable amplifying and transmitting means, controls an implanted pulse generator to turn on if a natural beat is delayed or missed and to turn off for a predetermined period after a natural beat occurs. Thus, Whenever the heart misses a natural beat, an artificial stimulating pulse is supplied. Even prior to Zacouto, Davies, in British Pat. No. 826,766 had suggested a pacer which turned on at random after the heart had missed several beats but was inhibited or turned off immediately after a natural beat occurred. Subsequently, Berkovits proposed a scheme in U.S. Pat. No. 3,345,990 for causing the heart to beat at a fixed rate by supplying an artificial stimulating pulse at exactly the same time as the missed natural beat should have occurred.

Among the disadvantages of the aforementioned prior types of pacers is that they compel the heart to beat at a fixed rate regardless of the physiological demands of the body. For example, when the subject is sleeping or involved in low physical activity, the heart rate naturally declines. Prior types of pacers sense the lower natural rate as indicative of missed or seriously delayed beats. The pacing pulse generator then turned on in response to this condition to stimulate the heart at a higher rate than is required by the physiological demands of the body.

This superfluous stimulation results in the subject experiencing an undesirable state of wakefulness and it has other disadvantages. Every unnecessary stimulating pulse consumes electric energy and causes the pulse generator's batteries to deplete sooner. The heart operates less efficiently than it would under the control of its own conductive system. Electrolysis of the heart electrodes is unduly accelerated by unnecessary stimulating pulses. Excess pacing may contribute to cardiac tissue damage.

SUMMARY OF THE INVENTION

An object of the invention is to provide an artificial heart pacer which has negative hysteresis, that is, which does not supply an artificial pacing pulse until the heart has dropped to a predetermined minimum beating rate and which then turns on to stimulate at a higher rate that is more consistent with the requirements of normal physical activity.

Another object of the invention is to provide a pacer which may be adapted for positive hysteresis, that is, which turns on the high fixed rate artificial pulse generator sooner after a natural beat has occurred than the time interval which would elapse between consecutive high rate artificial pulses.

How the foregoing and other more specific objects are achieved and the advantages of their achievement will appear from time-to-time throughout the course of the ensuing more detailed description of preferred embodiments of the invention.

In general terms, the new standby heart pacer comprises a means for detecting the presence or absence of either natural or artificially stimulated electric signals on the heart. The detected signals are processed and used to control an hysteresis circuit or memory which determines if the last heart beat was a natural or artificial. A fixed rate pacing pulse generator is normally biased off. If a predetermined time delay elapses after the last natural beat, the hysteresis circuit enables the pacing pulse generator to turn on and stimulate the heart one beat after the delay and then to stimulate at the intrinsic rate of the pacing pulse generator until the next detected natural pulse occurs and the hysteresis cycle is reset.

A more detailed description of the invention will now be given in reference to the drawings.

DESCRIPTION OF A PREFERRED EMBODIMENT

Figure 1:
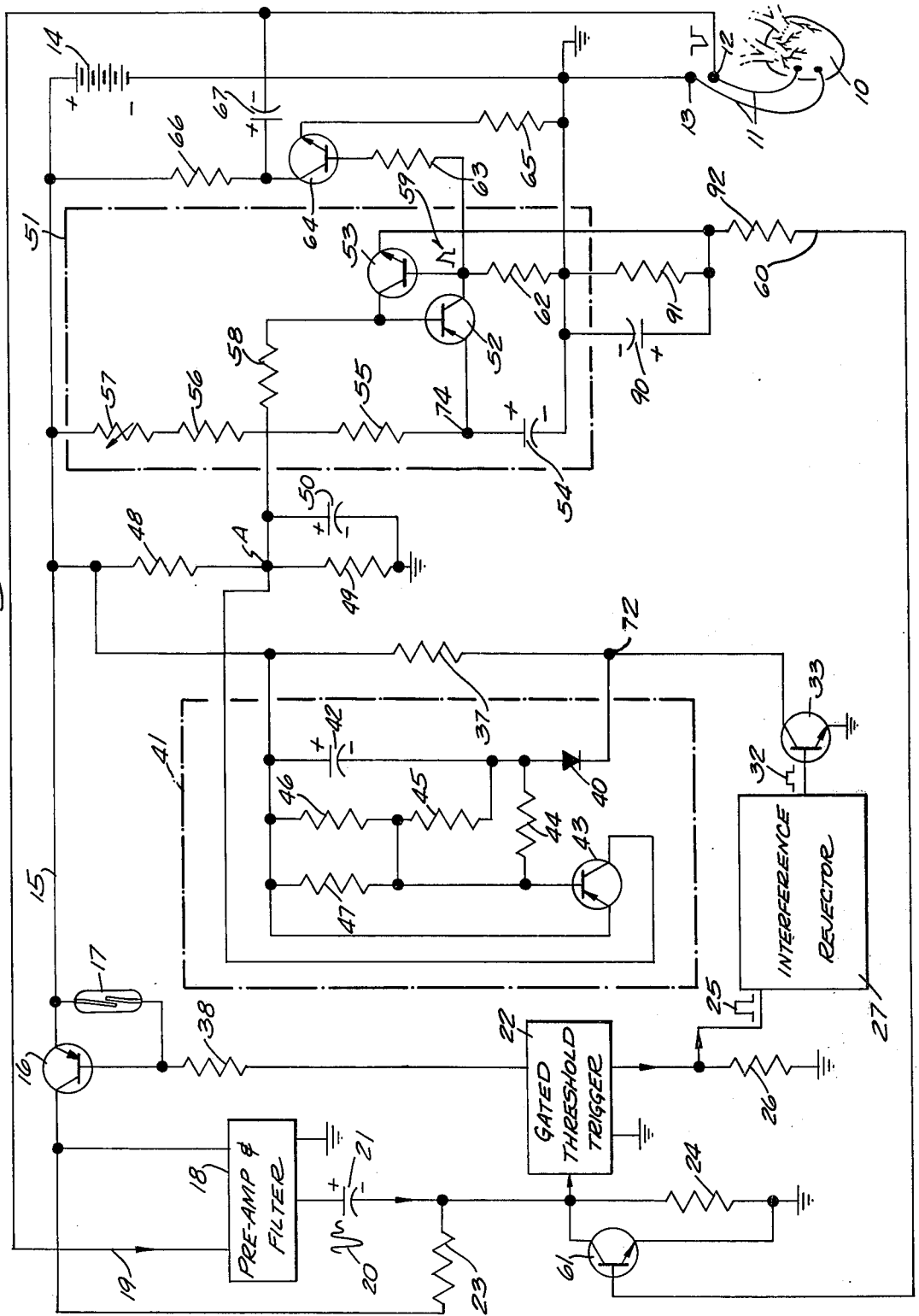
FIG. 1 is a circuit diagram of the new standby heart pacer.

At the far right in FIG. 1, one may see a heart 10 to which is connected a pair of leads 11 which connect to the output terminals 12, 13 of the standby pacer. Leads 11 may be a catheter running from the pacer through a blood vessel to the interior of the heart or they may run from the pacer through tissue to the myocardium where they are attached. In either case, leads 11 serve the dual purpose of delivering artificial pacing pulses to the heart and for detecting the presence of natural heart signals. Of course, separate leads could be used for detecting and delivering heart signals.

The remainder of the circuitry in FIG. 1 is adapted for being implanted in the body. The circuit elements are usually implanted in a solid epoxy resin and coated with body tolerant material, such as silicone rubber, a standard practice for pacer construction.

The pacer is powered by a mercury battery 14 which in this case has six cells and an initial terminal voltage of about eight volts. Near the left of the drawing, one may see that positive line 15 from the battery includes a transistor 16 which serves as a switch. The transistor has a base resistor 38. The emitter-to-base circuit of the transistor is shunted by a magnetically operable reed switch 17. When the pacer is in storage, reed switch 17 is normally closed so that the transistor is not forward-biased, in which case, power is cut off from some of the components in the pacer circuitry and they do not consume electric energy during this period. When the pacer in installed as a standby pacer, the reed switch 17 is in the normally open state removing the shunt across the emitter-to-base and placing transistor 16 in the conductive state. The conduction of transistor 16 supplies power to the detection circuitry, allowing the pacer to operate in the standby mode. Another purpose of transistor 16 is to permit it to be rendered nonconductive by closing reed switch 17 with a magnet when the pacer is implanted in the body. This converts the pacer to a free-running fixed rate pulse generator and allows the physician to determine whether the rate generator circuitry is working properly and the battery is at the proper voltage level. These determinations are made in conjunction with taking electrocardiographs.

The first stage in the pacer is shown in block form and includes a preamplifier and filter marked 18 which comprises signal detecting means. A line 19 runs from the filter to pacer output terminal 12. Detected heart waves are thereby introduced to the filter by way of conductor 19. The filter has a band-pass between 20 and 40 Hz. Each natural or artifically induced heart signal is rich in fundamental frequencies within this band-pass region. When a heart signal or R-wave is received, filter 18 is shocked and produces a ringing output signal of the form marked 20 on the output side of the filter. An alternating ringing signal 20 is produced by the filter regardless of whether the incoming R-wave signal from the heart is positive or negative. The filter is designed to clip large incoming signals, preventing signal distortion and phase shift in the following stages. Other means, not shown, could be used to produce a signal in response to electrical or mechanical action by the heart.

The ringing signal is a-c coupled through a capacitor 21 to a gated threshold trigger 22 which is shown in block form. The trigger is biased by a voltage divider comprising resistors 23 and 24. Trigger 22 is designed for being very sensitive to small imput signals, while providing good amplitude selectivity. For any positive swing of ringing signal 20, there is a single output pulse such as 25 delivered from trigger 22. The output pulse appears at the top of a resistor 26. It will appear later that trigger 22 is sometimes inhibited and produces no output signal when an artificial stimulating or pacing pulse is being delivered to the heart. Inhibition or gating of the signals is accomplished with a transistor gate 61 which will be described later.

Output pulses 25 occurring at the rate at which R-waves are being detected are delivered to an interference rejection circuit which is shown in block form and designated generally by the numeral 27. For brevity, the interference rejection circuit will hereafter be called a rejector and only its general functional characteristics will be described in this application.

Rejector 27 is analogous in one respect to a low-pass repetition rate filter which yields an output signal for input pulse rates associated with normal heart activity, excluding high repetition rate signals associated with certain types of interference, such as electric razors, electric drills and automobile ignition systems. However, the rejector is not frequency responsive but is pulse rate responsive. This example contemplates an output pulse from rejector 27 for input pulse rates ranging up to around 240 beats per minute. For present purposes, it is sufficient to know that input pulses 25 of sufficient amplitude and at a low enough rate will produce an output pulse 32. Thus, there is an output pulse 32 produced for every natural heart beat that occurs. These output pulses are furnished to the base of transistor 33 which conducts for the duration of every pulse 32. When transistor 33 conducts, it resets an hysteresis circuit as will be described.

Transistor 33 has its collector connected to the usual collector-resistor 37 which can be traced back to positive line. Its collector is also connected to the cathode of a diode 40 in the negative hysteresis circuit which is enclosed in dashed-dot lines and generally designated by the numeral 41. When transistor 33 conducts in response to the occurrence of a natural R-wave, it causes diode 40 to become forward-biased and to charge a capacitor 42 to a specific voltage level. The duration of pulse 32 is long enough to insure complete charging of capacitor 42 to the specific voltage level. The charging path for capacitor 42 begins at positive line and continues to diode 40 and the collector-to-emitter circuit of transistor 33 to negative ground. Whenever capacitor 42 is at a voltage above a certain level, it foward-biases the emitter-to-base circit of a transistor 43 in the hysteresis circuit and keeps it conductive. The bias voltage is developed across a network of resistors which are marked 44, 45, 46, and 47. Between natural heart beats or between conduction periods of transistor 33, capacitor 42 will gradually discharge through the network and transistor and cause transistor 43 to become nonconductive with the removal of forward-bias between the base and emitter of transistor 43 if natural heart beats do not occur frequently enough to keep sufficient voltage on capacitor 42. Note that the hysteresis period or time interval between a natural pulse and the time when the transistor 43 becomes non-conductive is predetermined and repeatable and that the pacing pulse generator will turn on at a definite time in relation to the last natural pulse.

The emitter-to-collector path of transistor 43 is shunted across a resistor 48 which is part of a biasing voltage divider that includes a series resistor 49. The collector of transistor 43 connects to a junction point A intermediate bias resistors 48, 49. When transistor 43 is conducting, resistor 48 is shunted and the potential at point A is substantially equal to positive line voltage. When transistor 43 becomes nonconductive as a result of transistor 33 not having conducted due to an excessively delayed or absent heart beat, the shunt is removed from biasing resistor 48 and point A goes more negative. Resistor 49 in the divider is paralleled with filter capacitor 50.

Attention is now invited to the pacing pulse generator which is enclosed in dashed-dot lines and designated generally by the reference numeral 51. The pacing pulse generator is biased off during conduction of transistor 43 when natural R-waves are occurring at a rate above a minimum that is compatible with physiological requirements of the subject. The pacing pulse generator includes two transistors 52 and 53. They are normally biased off and are turned on when point A goes negative provided there is forward-biasing voltage for the emitter-to-base path of transistor 52. Connected to the emitter of transistor 52 is a pacing pulse generator timing network including capacitor 54 which is charged through a series of resistors 55, 56 and an adjustable resistor 57. Capacitor 54 charges to substantially line voltage and remains at that voltage as long as point A remains relatively positive as it does when natural waves are occurring above an established minimum rate. When point A goes more negative, capacitor 54 in the charge state will supply the necessary current to forward-bias the emitter-to-base circuit of transistor 52 through a path which includes resistor 58. This also renders the emitter-to-collector circuit of transistor 52 conductive and causes a pulse 59 to appear on the collector. The pulse duration is about two milliseconds which is desirable for stimulating the heart. The latching voltage keeping this multivibrator circuit in conduction appears across resistor 58 and is additive to the bias voltage across resistor 48. The other transistor 53 also conducts when an artificial pacing pulse is delivered and the potential appearing on its emitter is applied through a resistor 92 and a conductor 60 to the base of the gating transistor 61 at the far left of the drawing. A filter network including parallel capacitor 90 and a resistor 91 prevent the emitter of transistor 53 from floating above ground potential while providing emitter impedance during the conductive state of transistor 53. The purpose of applying this signal to transistor 61 is to render it conductive and thereby inhibit the threshold trigger 22 so that it does not sense or respond to artificial pacing signals. When transistor 61 conducts, the top of resistor 24 is placed at ground potential and the bias is removed from the threshold trigger 22 so it produces no output pulse 25.

If the threshold trigger were not inhibited, artificial pacing pulses would result in pulses being passed through the rejector 27 and the hysteresis circuit 41 would be reset undesirably. Therefore, the inhibiting circuit provides selective feedback, selecting between natural and pace signals for processing by the threshold circuit 41. Capacitor 42 in the hysteresis circuit should only be recharged by the occurrence of a natural pulse because negative hysteresis calls for the pacing pulse generator being turned on only after a predetermined time interval has elapsed following occurrence of the last natural heart beat. In a commercial embodiment, the pacing pulse generator pulses are set at a rate of 71 per minute when it is made operative. However, the negative hysteresis circuit dictates that it shall not turn on until 1/60th of a minute or other chosen predetermined interval has elapsed following the occurrence of the last natural heart beat. The result is that the heart is permitted to change its rate in response to reduced physiological requirements from 71 beats per minute down to about 60 beats per minute before an artificial pulse is supplied. This is in contrast to prior art pacers in which made an effort to supply an artificial pacing pulse when there was a delay or absence of a natural pulse so that the heart would beat at a constant minimum rate at all times.

Output pulses 59 appearing on the collector of transistor 52 produce a signal voltage across a resistor 62 in the pacing pulse generator 51. This signal voltage is transmitted through a resistor 63 to the base of a transistor 64. Transistor 64 has a current limiting resistor 65 in its emitter circuit and a high value collector-resistor 66. Between pulses and between conduction intervals of transistor 64, a heart coupling capacitor 67 slowly charges through high resistance 66. The slow charge rate is insufficient to stimulate the heart. However, when a pulse is delivered to transistor 64, and it becomes conductive, capacitor 67 is discharged in a little more than 2 milliseconds and this results in sufficient current flow to stimulate one heart beat. This process is repeated as long as the pacing pulse generator is operating and the heart beats at the intrinsic rate of the pulse generator.

It should be noted that neither the output circuit including transistor 64 and coupling capacitor 67 nor the pacing pulse generator consume any more than leakage current when they are in their standby state. Once capacitor 54 in the pacing pulse generator is charged, it remains in that state until a natural heart beat is missed or delayed for more than one second or for any other chosen hysteresis period. This conserves battery life. Moreover, the fact that the heart can operate over a wider range of rates from above 71 beats per minute down to 60 beats per minute, or more or less depending on the chosen hysteresis period, without having any artificial pacing pulses injected, results in a further conservation of battery energy, reduces electrolysis at the electrodes and permits the heart to operate most efficiently under its natural conduction system for greater periods of time.

From the foregoing description it should be evident that in order to have the type of hysteresis which the device produces, there must be true inhibition of the heart signal sensing means, and there must be two independently controllable and different selectable time constants for the hysteresis and pacing pulse generator circuits. It must also be possible to introduce a pacing pulse at a repeatable fixed time after the last natural pulse has occurred.

The circuit in FIG. 1 is also readily adaptable to exhibit positive hysteresis. Positive hysteresis, as used herein, means that an artificial pacing pulse is delivered at a time following the last natural beat which is less than the period between the constant rate pulses which are produced by the pacing pulse generator 51.

Patients may benefit from a pacer which is specialized with positive hysteresis if they are subject to arrhythmias or irregular heart rates. In such cases, it is sometimes possible to capture the heart rate and make it more regular by injecting an artificial pacing pulse at a predetermined early time following occurrence of the last natural heart stimulus.

Figure 3:
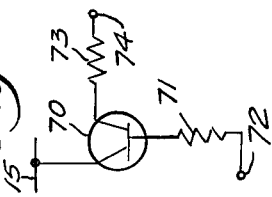
FIG. 3 is a circuit diagram of a modification of the new standby heart pacer of FIG. 1.
Figure 2:
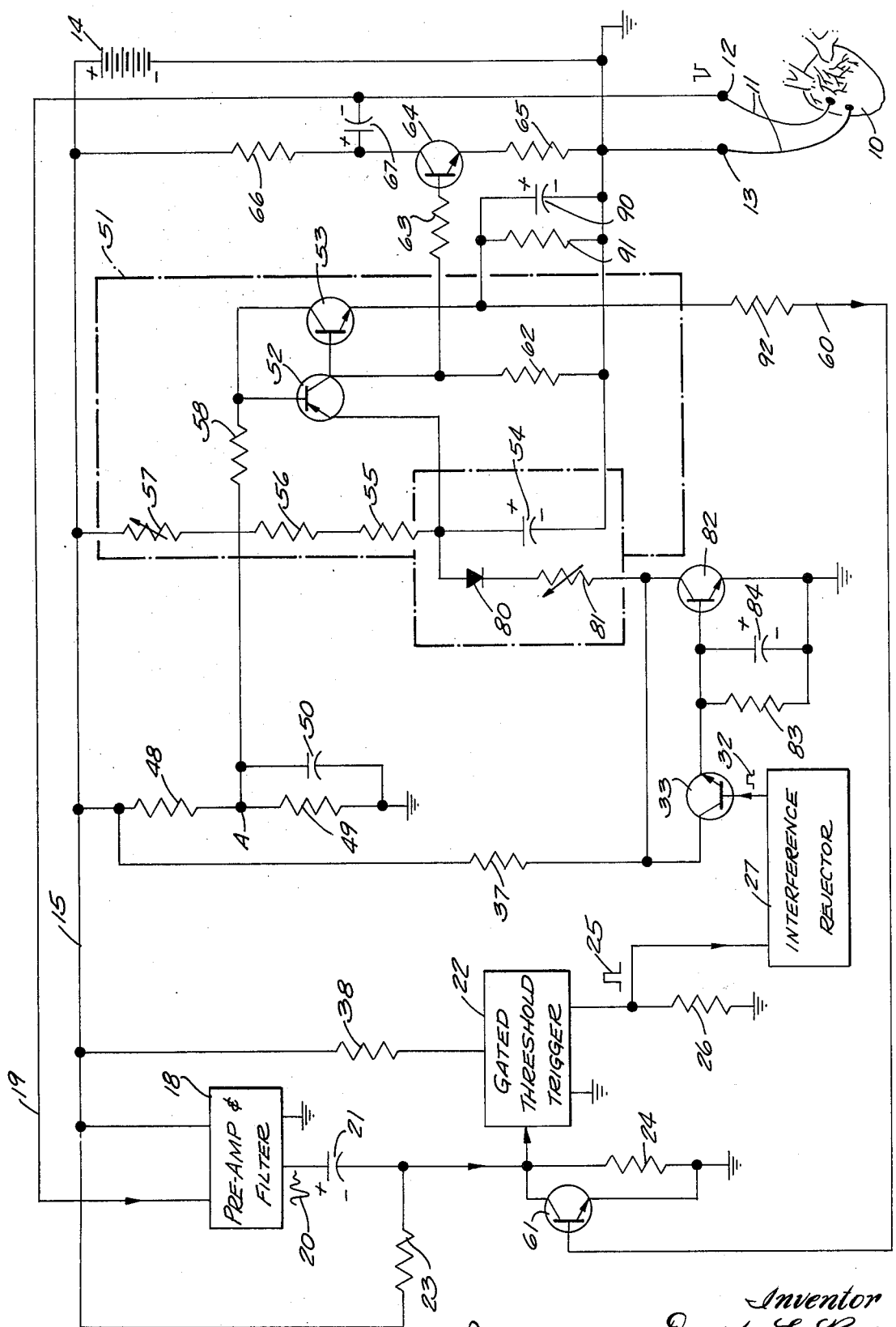
FIG. 2 is an alternative form of standby pacer incorporating some of the features of the preceding figures and including some additional features.

The components which may be added to adapt the particular pacer of FIG. 1 for positive hysteresis are depicted in FIG. 3. The circuit includes a transistor 70 which has a base resistor 71 connected to junction point 72 coming out of the negative hysteresis circuit. The emitter of transistor 70 is connected directly to positive line and its collector is connected through a resistor 73 to a junction point 74 and capacitor 54 in the pace pulse generator timing network. Thus, it is evident that upon occurrence of a natural pulse and concomitant conduction of transistor 33, transistor 70 will also conduct and cause capacitor 54 in the pacing pulse generator to charge more rapidly than it would normally through its charging circuit comprising resistors 55, 56, and 57. At the same time, bias voltage is shunted from resistor 48 of transistor 43, rendering the rate circuit nonresponsive until the hysteresis circuit has timed out which will be after a shorter period than the period between pace pulses. This premature charging advances the time when transistor 52 in the pacing pulse generator becomes conductive and the heart will be stimulated to beat earlier as determined by the hysteresis circuit and not exclusively by the pace pulse generator timing circuit Attention is now invited to FIG. 2 in connection with which alternate forms of positive and negative hysteresis will be described. The device in FIG. 2 is primarily intended for external pacing, that is, where the pacer is located outside of the body and the heart is stimulated through a transvenous catheter entering the heart chambers. On the other hand, the device in FIG. 1 is usually implanted in the body.

In FIG. 2, parts that have the same function as in the preceding figure, are given in the same reference numerals.

In FIG. 2, the signal is processed in the same manner as it was in the circuitry of FIG. 1 up to the point of transistor 33 at the output of interference rejector 27. This is, every time a natural R-wave of sufficient amplitude occurs, a pulse gets through the interference rejector and causes transistor 33 to become conductive. Meanwhile, timing capacitor 54 in pacing pulse generator 51 has been charging through timing resistors 57, 56, and 55. The timing capacitor 54 voltage is, therefore, increasing toward the point where transistor 52 will be forward-biased producing a pace pulse. When transistor 33 conducts, however, upon occurrence of a natural heart beat, capacitor 54 discharges to ground through a diode 80, an adjustable resistor 81, the collector-to-emitter path of transistor 33, and the Darlington connected or parallel transistor 82. Transistor 82 becomes forward-biased simultaneously with transistor 33 by virtue of a forward-biasing potential being developed across a resistor 83 in parallel with a filter capacitor 84. It is evident, then, that whenever a natural heart wave occurs, both transistors 33 and 82 conduct and cause whatever charge has accumulated on timing capacitor 54 to be discharged prematurely to ground through a path starting with diode 80. Although this is wasteful of battery energy, it is tolerable in a device that is used primarily external of the body and in which batteries may be replaced regularly without convenience.

Discharging capacitor 54 prematurely, prohibits the pacing pulse generator from being turned on which is equivalent to saying that transistor 52 does not become forward-biased. After occurrence of a natural pulse has discharged capacitor 54, it begins to recharge slowly and if it reaches peak charge before expiration of the hysteresis time, it will forward-bias transistor 52 and provide an artificial pacing pulse to the heart. This is so because the voltage on capacitor 54 will be sufficient to overcome the reverse-biasing potential which exists at point A.

The combination of diode 80 and adjustable resistor 81 in conjunction with capacitor 54, comprises an hysteresis circuit for this device. One may see that if the value of resistor 81 is set relatively low, capacitor 54 will encounter a low impedance path and discharge substantially completely whenever a natural R-wave is detected. When the rate generator provides an artificial pulse, capacitor 54 discharges through emitter-base of transistor 52 and the parallel paths established by transistors 53 and 64. In this case, capacitor 54 will discharge to a low voltage level but some residual voltage will remain on capacitor 54. This low impedance discharge will produce a lower residual voltage on capacitor 54 and, therefore, will take a longer time to recharge. Negative hysteresis prevails if the recharge time is greater than the time interval between successive fixed rate pulses from the pacing pulse generator. Thus, when a natural beat occurs, there may be a delay of any chosen amount such as that corresponding with sixty heart beats per minute before a pacing pulse is delivered. Again, the heart rate can, for example, drop below the intrinsic rate of the pacing pulse generator down to a lower limit of 60 pulses per minute, or more or less depending on the chosen hysteresis delay, before there is any artificial stimulation.

By setting resistor 81 to a very low value, the difference between the pacing pulse rate and the minimum natural rate can be extended. As resistor 81 is increased in value, there is a shorter hysteresis period between the occurrence of a natural beat and the time when a pacing pulse is delivered.

As the value of resistor 81 is increased even further, it is possible to obtain positive hysteresis, going through a state when the hysteresis period will equal the pace period. This results from the fact that a high value for resistor 81 prohibits capacitor 54 from discharging to a very low level after the last natural heart beat and it recharges more rapidly as a result of starting from a higher level following the last natural beat. Resistor 81 can be so adjusted that an artificial pacing pulse is delivered very shortly after the last natural pulse so that the heart rate is captured by the pacing pulse generator. In this design, the hysteresis interval will vary proportionately with variations that are made in the pacing pulse period.

The external standby pacer unit may be employed after a subject has had an heart attack and a medical determination is being made as to the best type of implantable pacer to install, if any. The external unit, therefore, has adjustments which are not present and could not be profitably used on an implanted unit.

In summary, a standby pacer has been described which features negative and positive hysteresis. The hysteresis means are characterized as providing a first stimulating pacing pulse at a definite time following occurrence of the last natural pulse and always in synchronism with or in proper phase relationship with the timing of the artificial pulse generator. The new pacer is capable of delivering a single pacing pulse if only one heart beat is unduly delayed or missed and it will continue to deliver pacing pulses at the intrinsic rate of the pacing pulse generator until a natural pulse reoccurs. It will turn on whenever the heart rate drops below a predetermined minimum and, therefore, usually paces artificially when there is heart malfunction rather than change of physiological demand. It turns off when the heart rate, even for a single beat, is at an acceptable level. When it does turn on, it paces the heart at a high enough rate to permit the subject to carry on essentially normal physical activity.

Although illustrative embodiments of the new concepts in heart pacers have been described in considerable detail, such description is to be treated as purely illustrative rather than limiting, for the invention may be variously embodied and is to be limited in scope only by interpretation of the claims which follow.

I claim:

1. A standby heart pacer comprising:
   a. a selected-rate pace pulse generator having output terminals adapted to be connected to the heart and to stimulate with pace pulses the heart at regular time intervals in the absence of natural heart action, b. power source terminals,
c. a timing network included in said pace pulse generator and adapted to set the time period between pace pulses, said timing network being connected with a power source terminal,
d. detector means directly connected to at least one output terminal and responsive to heart activity signals to produce corresponding detector output signals,
e. means responsive to said pace pulse generator pace pulses to produce a detector output signal inhibiting signal on occurrences of a pace pulse,
f. a hysteresis means interposed between said detector means and said pace pulse generator timing network said hysteresis means being actuated by detector signals in the absence of an inhibiting signal, to set a single repeatable time interval between detection of natural heart activity signals and the generation of a first pace pulse independently of the regular time interval between pace pulses produced by said generator, the instant at which said hysteresis device is set being coincident with the natural heart activity signal,
g. means controlled by said hysteresis means for preventing said timing network in said pace pulse generator from producing a pace pulse for the duration of said repeatable time interval and for enabling production of a pace pulse at the end of said repeatable time interval, whereupon ensuing pace pulses at regular time intervals are determined by said pace pulse generator timing network and continue until a natural heart activity signal resets the repeatable time interval in said hysteresis device, and coincidentally inhibits said pace pulse generator for said repeatable time interval.

2. The invention set forth in claim 1 wherein:
a. said hysteresis device includes an hysteresis timing capacitor and means for charging the same to a predetermined voltage level from a power source terminal in response to occurrence of an uninhibited detector signal corresponding to a natural heart activity signal,
b. resistor means connected across said hysteresis timing capacitor to discharge the same to a predetermined lower voltage level in a repeatable time period different than its charging period,
c. bias means coupled with said pulse generator timing means and including means which change its biasing state in response to said hysteresis capacitor attaining either of its predetermined voltage levels to thereby define a predetermined time interval between said hysteresis capacitor voltage levels,
d. said pace pulse generator including means responding to one biasing state of said bias circuit by turning on and producing a pace pulse under the control of its said timing network and responding to the biasing state existing during the time between said predetermined voltage levels by preventing said pulse generator from turning on.

3. The invention set forth in claim 1 wherein:
a. said hysteresis means includes an hysteresis timing capacitor and a discharge resistor means connected thereto, and
b. power source terminals and a first switch means connected in a series circuit with said hysteresis timing capacitor, said series circuit being connected to said source terminals and said switch means being rendered conductive in response to a detector signal in the absence of an inhibiting signal to charge the hysteresis capacitor to a predetermined voltage level from said power source terminals,
c. said discharge resistor means being connected across said hysteresis timing capacitor for discharging said hysteresis capacitor toward a predetermined lower voltage level after it has been charged to a predetermined voltage level,
d. a second switch means connected to said discharge resistor means and adapted to be rendered conductive when a bias voltage developed in said discharge resistor means is above a predetermined level,
e. a bias voltage divider across a part of which said second switch means is shunted to maintain the voltage on an intermediate point in the divider at one voltage level when said second switch means is conductive and at another level when it is not conductive,
f. the aforesaid timing network in said pace pulse generator including a timing capacitor and a charging circuit therefor, the voltage differential between the voltage on said timing capacitor and the voltage on said intermediate point in said bias voltage divider being effective to keep said pace pulse generator turned off when said second switch means is conductive, the absence of a natural heart beat for a predetermined interval causing the hysteresis capacitor to attain its predetermined lower voltage level to render the second switch means nonconductive and change the voltage at said intermediate point to said other level whereupon said voltage differential no longer is effective to keep said pace pulse generator turned off, and the voltage on said timing capacitor turns on the pace pulse generator, said pace pulse generator then supplying pace pulses at its regular time intervals to the heart until a natural heart beat occurs to reset said hysteresis device.

4. A standby heart pacer with negative hysteresis comprising:
a. a selected-rate pace pulse generator having output terminals which are adapted to be connected to the heart for electrically stimulating it on demand,
b. power source terminals,
c. a timing network for said pace pulse generator including a timing capacitor and a charging circuit for charging said timing capacitor from said power source terminal to a predetermined level within a selected period of time,
d. a bias voltage divider connected to said pace pulse generator and having an intermediate point, said pace pulse generator being adapted to turn on to deliver a pulse to the heart when there is a predetermined difference between the voltage at said intermediate point and the voltage on said timing capacitor,
e. detector means connected to an output terminal and adapted to be responsive to produce an output signal corresponding with either a pace pulse or a natural heart signal,
f. a gate means connected with said detector means to receive said output signals and to pass said signals when natural heart signals occur and to inhibit said signals from passing when pace pulse signals occur, g. means controlling said gate means in response to occurrence of a pace pulse signal to inhibit passing of said signals, h. a first switch means adapted to be rendered conductive in correspondence with natural heart signals, in the absence of signal inhibition, i. a negative hysteresis device including a capacitor that is charged to a first predetermined voltage level from a power source terminal through said first switch means each time a natural heart signal occurs, j. a network including means connected to said hysteresis device capacitor for discharging the same to a second predetermined voltage level within a repeatable time interval after each natural heart signal is detected, k. a second switch means having a control electrode connected to said discharge network and adapted to be rendered conductive at one predetermined voltage level of the hysteresis device capacitor and nonconductive at the other predetermined voltage level, said second switch means being adapted to control the voltage state of said intermediate point in said bias voltage divider such that said pace pulse generator is turned on to deliver an artificial pace pulse to the heart if a natural heart signal does not occur during said repeatable time interval of said network which is chosen to be greater than the interval between ensuing selected-rate pulses from the pace pulse generator.

5. A standby pacer with positive hysteresis comprising:

a. a selected-rate pace pulse generator having output terminals which are adapted to be connected to a heart for electrically stimulating it, b. a timing circuit for said pace pulse generator including a timing capacitor and a charging circuit for charging said timing capacitor to a predetermined voltage level within a selected period of time, said pulse generator including means responsive to turn on said generator for delivering a stimulating pulse to the heart when said timing capacitor attains said predetermined voltage level and another condition is met, c. a bias voltage divider means having an intermediate point connected to said pace pulse generator, said pace pulse generator turning on to deliver a stimulating pulse to the heart under said another condition that there is a predetermined voltage difference between the voltage on the timing capacitor and at said intermediate point, d. a detector means adapted to be connected to the heart and responsive to produce an output signal when either a natural heart beat or a pace pulse is detected, e. a gated threshold trigger means including means responsive selectively to signals from said detector means to cause said trigger means to produce corresponding detector output signals when said trigger means is not inhibited, f. a means responsive to occurrence of a pace pulse signal on said output terminals to inhibit said gated threshold trigger, g. a discharge circuit for said capacitor including impedance producing means and switch means having main electrodes and a control electrode connected to receive detector output signals which are coincident with the natural heart beats and said switch means becoming conductive in response to said detector output signals to thereby partially discharge said timing capacitor to a level that is below said predetermined level so that said timing capacitor is recharged, after said switch means has been conductive, to said predetermined voltage level in a shorter time than would occur in the absence of a natural heart beat, h. whereupon a stimulating pulse may be delivered to the heart to stimulate it after a natural heart beat has occurred within an interval that is less than the time between pace pulses from the generator.

6. A standby heart pacer comprising:

a. a normally inhibited selected-rate pace pulse generator having output terminals adapted to be connected to a heart for stimulating it to beat if a natural beat is missed or delayed for an undesirable period, b. power source terminals, c. a pace pulse generator timing network including a timing capacitor and resistor means through which the capacitor is charged at a selected rate from a said power source terminal, said pulse generator including means responding to the voltage on the timing capacitor attaining a predetermined upper level to turn on said pulse generator to discharge the timing capacitor to a predetermined level and to cause a stimulating pulse to be delivered to the heart if a natural heart beat does not occur before said timing capacitor attains said predetermined level, d. hysteresis means connected to said timing capacitor and comprising a discharge circuit including an hysteresis control resistor and a switch means in series therewith and with said timing capacitor, said switch means having a main conduction path and a control electrode, said main path discharging said timing capacitor to a different voltage level than it would normally attain through pace pulse generator operation, e. a detector means coupled with said output terminals and responsive to produce an output signal when a natural heart beat or a pace pulse is detected, f. a gated threshold trigger means including means responsive selectively to signals from said detector means to produce corresponding detector output signals when said trigger means is not inhibited to prevent such detector output signals when said trigger is inhibited, g. a gate means responsive to occurrence of a pace pulse signal by inhibiting said gated threshold trigger, said trigger not being inhibited when a natural heart beat occurs, h. the aforesaid control electrode of said switch means being connected with said gated threshold trigger means to receive signals therefrom when said gated threshold trigger is not inhibited to thereby render said switch means conductive to discharge said timing capacitor to said different voltage level that depends on the resistance of said hysteresis control resistor whenever a natural heart beat occurs, thus setting a new starting time for recharging said timing capacitor so that the time interval between a natural heart beat and a pace pulse is different than the time interval between pace pulses in the absence of a natural heart beat.

7. The invention set forth in claim wherein:

a. said discharge time constant through said hysteresis circuit is of such length as to set the final voltage on said timing capacitor at such level that the recharge time is short, whereby a first pace pulse is provided to the heart in the absence of a natural beat at the end of a time interval which is shorter than the interval between pulses from the pace pulse generator.

8. The invention set forth in claim 6 wherein:
a. said discharge time constant through said hysteresis circuit is of such length as to set the final voltage on said timing capacitor at such level that the recharge time is long, whereby a first pace pulse may be provided to the heart in the absence of a natural beat at the end of a time interval which is longer than the interval between pace pulses from the pace pulse generator.

9. A standby heart pacer comprising:
a. a normally inhibited selected-rate pace pulse generator for producing artificial heart stimulus signals and having output terminals adapted to be connected to a heart for stimulating it to beat at a predetermined rate which is no less than is commensurate with normal physical activity of the body.
b. an hysteresis means connected to said pace pulse generator which means has two states, one of which states removes the inhibition from the pulse generator and the other of which states maintains the inhibition, said hysteresis means including means for inhibiting said pulse generator,
c. detector means adapted to detect through said output terminals the occurrence of natural stimulus signals on the heart which cause the heart to beat and artificial pace pulse signals on the heart which also cause the heart to beat, said detector means selectively controlling the state of the hysteresis means depending on whether an artificial or natural heart beat is detected by said detector means,
d. said hysteresis means including means responding to a detected natural heart beat by said detector means by setting the start of an exclusive repeatable hysteresis delay period during which delay period said hysteresis circuit is maintained in the state which actuates the pace pulse generator inhibiting means and afrer which delay period say hysteresis circuit changes state to deactivate said pace pulse generator inhibiting means, whereupon a first artificial pace pulse is delivered to the heart substantially coincidentally with the end of said single delay period,
e. the repeatable hysteresis delay period being different than the interval between consecutive pace pulses from the generator whereby the heart may beat continually in response to natural signals in a physiologically acceptable range of rates between the rate of said artificial pulse generator and a lower limit rate corresponding with said delay period before the heart is stimulated by a first artificial pace pulse.

* * * * *

UNITED STATES PATENT AND TRADEMARK OFFICE
CERTIFICATE OF CORRECTION

PATENT NO. : 4,030,510

DATED : June 21, 1977

INVENTOR(S) : David L. Bowers

It is certified that error appears in the above-identified patent and that said Letters Patent are hereby corrected as shown below:

Column 12, Line 48, after "inhibited" insert --and--.

Column 12, Line 68, after "Claim" insert --6--.

Column 14, Line 17, "afrer" should read --after--.

Signed and Sealed this

Eleventh Day of October 1977

[SEAL]

Attest:

RUTH C. MASON
*Attesting Officer*

LUTRELLE F. PARKER
*Acting Commissioner of Patents and Trademarks*